United States Patent [19]

Dewey et al.

[11] 4,025,628
[45] May 24, 1977

[54] CONTROL OF BOVINE MASTITIS

[75] Inventors: Lloyd G. Dewey, Roseville; James J. Jezeski, New Brighton, both of Minn.

[73] Assignee: H. B. Fuller Company, St. Paul, Minn.

[22] Filed: Sept. 22, 1975

[21] Appl. No.: 615,282

[52] U.S. Cl. .............................................. 424/249
[51] Int. Cl.$^2$ ...................................... A61K 31/53
[58] Field of Search ................................... 424/249

[56] References Cited

UNITED STATES PATENTS

| | | | |
|---|---|---|---|
| 3,072,654 | 1/1963 | Vazopolos | 424/249 |
| 3,293,188 | 12/1966 | Brown et al. | 424/249 |

OTHER PUBLICATIONS

Bloomfield–Chem. Abst., vol. 80(1974), p. 100, 183g.

Primary Examiner—Sam Rosen
Attorney, Agent, or Firm—Thomas M. Meshbesher

[57] ABSTRACT

A powdered, storage stable, effervescent formulation readily dispersible in water and containing a watersoluble chlorinated cyanurate, such as sodium dichloroisocyanurate, is mixed with water to provide a stable, slightly acid to neutral, non-irritating aqueous liquid having about 3,000 to 7,000 ppm titratable chlorine which is used as a teat dip for hygienic control of bovine mastitis.

9 Claims, No Drawings

CONTROL OF BOVINE MASTITIS

This invention relates to a method for hygienic control of bovine mastitis. In another aspect, it relates to a teat dip liquid comprising a stable aqueous dispersion of titratable chlorine useful in the prophylaxis of bovine mastitis.

Mastitis is the most costly dairy cattle disease confronting the dairy farmer. It leads to reduced milk production and a lowered quality of milk from adulteration by the products of udder inflammation. Based on a number of studies, it has been estimated that more than half of the dairy cows have one or more quarters subclinically infected with bacteria typically associated with mastitis. The U.S. National Mastitis Council concluded that 95% of mastitis is caused by the pathogenic bacteria *Staphylococcus aureus* and *Streptococcus agalactiae*. Most infections enter through the teat canal and are believed to result from contamination by milk, dung, or mud after milking and can be spread from cow to cow during the milking process.

Several hygienic techniques have been proposed or used in the past for controlling mastitis, including the use of a teat dip for the purpose of destroying or reducing contaminating pathogens at the teat apex and thus controlling infection of the teat canal and the spread of pathogens from one quarter to another or from cow to cow. Emollients, such as glycerine, lanolin, polyvinylpyrolidone, and sorbitol have been used in conjuction with some teat dips to alleviate irritation caused by such dips or help heal chaps, lesions or sores. However, the teat dips proposed or used heretofore have not fully met the need for a practical mastitis control. For example, an aqueous 4% solution of sodium hypochlorite (e.g., "Chlorox"), containing 40,000 to 45,000 ppm titratable chlorine, has to be kept in a dark cool place and it has been reported as irritating or causing sores or lesions in some cases, is not stable in the presence of glycerine and lanolin emollients and other organic matter, is not effective in the presence of milk, and many milkers complain of its effect on their hands.

A year or more ago, a tabletted formulation, containing sodium dichloroisocyanurate, was sold for a limited time (as "Monarch Teat Tabs") for control of mastitis, the tablet consisting of 32 weight % each of sodium dichloroisocyanurate, sodium bicarbonate, and sodium bisulfate, 4 weight percent "Carbowax" 440 polyoxyethylene glycol, and 3 weight percent sodium benzoate. One such tablet (ca 6 grams) dissolved in 2 liters of water provided an aqueous teat dip having a pH of about 6.7 and about 600 ppm titratable chlorine but the tablets were found to be unstable under some ambient storage conditions and the resulting teat dip was found to be not as effective as desired in killing the pathogenic bacteria.

Briefly, according to this invention, hygienic control of bovine mastitis is provided by using as a teat dip a slightly acid to neutral (or nearly neutral), stabilized aqueous liquid having as its active material about 3,000 to 7,000 ppm, preferably about 5,000 ppm, titratable chlorine produced by dispersing in water a powdered, storage stable, effervescent formulation containing water-soluble chlorinated cyanurate, such as sodium dichloroisocyanaurate.

The chlorinated cyanurates, used as a source of titratable chlorine in this invention, can be expressed by the general formula

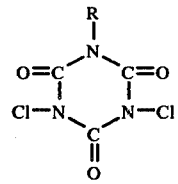

where R is hydrogen, chlorine, potassium or sodium. Compounds of this formula are 1,3,5-trichloro-s-triazine-2,4,6-trione, 1,3,-dichoro-s-triazine-2,4,6 (5H)-trione, 1-potassium-3,5-dichloro-s-triazine-2,4,6-trione, and 1-sodium-3,5-dichloro-s-triazine2,4,6-trione. The latter compound (referred to herein as by its common name, sodium dichloroisocyanurate) is the preferred chlorinated cyanurate used in this invention because of, inter alia, its high solubility in water, and the invention will be illustrated by it. The chlorinated cyanurates are used in this invention in their non-hydrate form, the dihydrate of sodium dichloroisocyanurate having undesirable instability.

Sodium dichloroisocyanurate, $(C_3N_3O_3Cl_2)Na$, is a somewhat complex crystalline compound (commercially sold, for example, under the trade marks "ACL-60" and "CDB-63"). This compound theoretically contains approximately 60% available chlorine, practically all of which is available when the compound is dissolved in water. (In contrast, normally available sodium hypochlorite solutions contain only about 6 to 12% available chlorine). Sodium dichloroisocyanurate per se readily dissolves on the order of 23 g/100 ml in water at 25° C and a pH of 7–8, a 1% solution having a nearly neutral pH, e.g., about 6.0 to 7.2. In hydrolyzing in water, the compound releases chlorine, which reacts with water to provide titratable chlorine and cyanuric acid; it's been used for many years in swimming pool water (e.g., see U.S. Pat. Nos. 3,342,674 and 3,488,420). Sodium dichloroisocyanurate has been compounded with carbon-dioxide producing adjuvant to provide tablets used to make aqueous solutions containing relatively low concentrations (e.g., 100, 150, and 1200 ppm) available chlorine and useful for bactericidal purposes such as denture cleaning, bleaching, sterilizing, and disinfecting (see British Patent Specification 1,165,098 and U.S. Pat. No. 3,120,378).

The sodium dichloroisocyanurate (and other chlorinated cyanurates) used in this invention to provide an aqueous liquid containing titratable chlorine is used in its powdered form and blended with powdered, inert, water-soluble carbon dioxide-producing adjuvant, chlorinated paraffins, and, optionally and preferably, with a compatible emollient such as sorbitol and poly(N-vinylpyrrolidone) (such as disclosed in U.S. Pat. No. 2,739,922 and commercially available as "PVP K-30"), or mixtures of such emollients, to prevent or minimize chapness of the teats. The powdered form of the formulation is an advantage, for example, as compared to sodium hypochlorite solutions, in that it reduces handling and shipping of water, it is stable and need not be kept in the dark, and it can be stored at ambient temperatures, without signficant decomposition even at elevated ambient temperatures, e.g. 40° C.

The carbon dioxide-producing adjuvant can be a combination of alkaline and acid materials such as commonly used in pharmacology to effect effervesence and agitation when such materials are dissolved in water, thereby providing a means for quickly dispersing the formulation in water. The effervescent adjuvant can be a combination of one or more non-toxic acids or salts thereof, such as citric acid, maleic acid, ascorbic acid, fumaric acid, tartaric acid, potassium acid tartrate, monobasic sodium phosphate, and sodium bisulfate, together with a non-toxic alkali metal carbonate or bicarbonate, such as sodium bicarbonate. A particularly useful carbon dioxide-producing adjuvant is a combination of monobasic sodium phosphate and sodium bicarbonate. The relative amounts of the carbon dioxide-producing adjuvant and acid and alkaline components thereof in the powdered formulation of this invention are such that sufficient carbon dioxide is evolved to aid the rapidity with which the formulation disintegrates and disperses in water.

A pH buffer, such as sodium sulfate, can be included in the formulation in an amount (e.g., 5 to 40 wt.%) sufficient to maintain the desired pH of the resulting aqueous teat dip.

The relative amount of the chlorinated paraffin component in the formulation is such that it ensures stability of the formulation during its preparation and storage prior to use in that the chlorinated cyanurate component does not decompose prematurely and release its chlorine, the chlorinated paraffin serving in a sense as a barrier between the cyanurate granules and the other components in the formulation. Typically the amount of chlorinated paraffin will be up to about 1 or 2 wt.% of the powdered formulation. The chlorinated paraffins generally will be normally liquid, contain 30 to 60 wt.%, typically 40 wt. %, chlorine, and are made by chorination of paraffins, which generally are paraffin waxes that are predominantely straight chain with 18 to 26, typically 20 to 23, carbon atoms (e.g., see Canadian Patent 649,130). Useful commercially available chlorinated paraffin products for this purpose are "Chlorowax LV" (which is preferred) and "Chloroflo 40", each containing 40 wt.% chlorine and having the average empirical formulas $C_{22}H_{44}Cl_6$ and $C_{20}H_{37}Cl_6$, respectively. The chlorinated paraffins are insoluble in water and so the resulting admixture of the powdered formulation of this invention is a somewhat hazy aqueous dispersion, though the active material of the formulation, viz. the chlorinated cyanurate, is completely dissolved in the water.

The compounded formulations of this invention will generally contain the equivalent of about 10 to 22 wt. % chlorine, bonded in the form of the chlorinated cyanurate component. The relative amounts of the components in the formulation generally are 15 to 40 wt. %, preferably about 18 to 36 wt. % chlorinated cyanurate; 15 to 50 wt. %, preferably about 30 to 50 wt. %, carbon dioxide-producing adjuvant, the latter generally being made up of 30 to 95 wt. %, preferably about 75 to 85 wt. %, acid or acid salt component and 5 to 70 wt. %, preferably about 15 to 25 wt. %, carbonate or bicarbonate component; 0.1 to 5 wt. %, preferably 0.5 to 2 wt. % chlorinated paraffin; and 0 to 30 wt. %, preferably 10 to 25 wt. %, emollient, such as 5 to 15 wt. % each of sorbitol and polyvinylpyrrolidone.

Table I shows a number of illustrative powdered formulations of this invention and the pH and titratable chlorine concentration of the teat dip solutions prepared therefrom.

Table I

| Formulation | A | B | C | D | E | F | G[e] |
|---|---|---|---|---|---|---|---|
| Ingredients, wt. % | | | | | | | |
| Sodium dichloroisocyanurate[a] | 17.9 | 17.9 | 17.9 | 35.8 | 35.8 | 35.8 | 32.0 |
| Sodium sulfate | 7.3 | 18.7 | 39.2 | 5.2 | 13.2 | 27.7 | 16.5 |
| Monobasic sodium phosphate | 42.5 | 35.2 | 17.7 | 30.0 | 25.0 | 12.5 | 12.0 |
| Sodium bicarbonate | 11.3 | 7.1 | 4.2 | 8.0 | 5.0 | 3.0 | 28.5 |
| Chlorinate paraffin[b] | 1.0 | 1.0 | 1.0 | 1.0 | 1.0 | 1.0 | 1.0 |
| Polyvinylpyrrolidone ("PVP K-60") | 10.0 | 10.0 | 10.0 | 10.0 | 10.0 | 10.0 | 10.0 |
| Sorbitol (crystalline) | 10.0 | 10.0 | 10.0 | 10.0 | 10.0 | 10.0 | 0 |
| Teat dip solution[c] | | | | | | | |
| Titratable chlorine[d], ppm. | 3173 | 3264 | 3226 | 6452 | 6452 | 6452 | 6170 |
| pH | 6.45 | 6.25 | 6.20 | 6.35 | 6.20 | 6.15 | 7.40 |

[a] Formulations A through F used "ACL-60" and Formulation G used "CDB-63".
[b] Formulations A through G used "Chlorowax LV".
[c] Each solution was made by mixing about 30 g of the Formulation in 1 liter water (ph 7.25, hardness 5 grains/gal.) at 72–74° F with vigorous shaking. The listed pH and ppm. chlorine values were determined within 5–30 min. after makeup of solution.
[d] Determined by titration with 0.1N sodium thiosulfate (Standard Methods for Examination of Dairy Products, 13th Edition, American Public Health Assn., p. 223, 1972).
[e] A Formulation like G when mixed in the amount of 16 g in 1 liter of water produced a solution with 3120 ppm. titratable chlorine and a pH of 7.3.

The powdered formulation of this invention can be prepared by thoroughly mixing or blending the components of the formulation to produce an intimate blend thereof. The powdered components will typically have a granule or particle size such that 97 to 98% pass through a U.S. Standard Sieve No. 20 screen (with openings of 0.840 mm) and are retained on a No. 100 and/or No. 200 screen (having openings of 0.149 and 0.074 mm, respectively). Generally, the carbon dioxide-producing components are mixed first, the emollient (if used) is then mixed in, followed by the chlorinated paraffin component, and the chlorinated cyanurate component added and mixed in last. The resulting powdered (or granulated) formulation can then be packaged in sealed containers.

The amount of powdered formulation to be mixed with water to produce the teat dip of this invention will depend on the quantity of test dip needed, i.e., the size of the herd of cows to be treated, and the desired concentration of titratable chlorine (i.e., 3,000 to 7,000 ppm) of the teat dip. A convenient and practical way of packaging will be to fill a sealable envelope or packet made of relatively moisture and gas impermeable paper, such as foil-paper laminates, with the requisite amount of the formulation which when added to the requisite amount of water will produce the requisite amount of teat dip having 3,000 to 7,000 ppm titratable chlorine. For example, a packet can be filled with 30 grams of formulation E of Table I and that amount added to about 1 liter of water to provide a liter of teat dip having an initial pH of 6.0 to 6.2 and about 6,500 ppm titratable chlorine; this teat dip can be used for two consecutive milkings and at the time of the second milking (when the teat dip is 12–14 hr. old) it will have about 5,000 ppm titratable chlorine.

The rate of dispersion of the powdered formulations of this invention is extremely fast, e.g., 30 seconds or less; for example, 30 grams of any of formulations A through F of Table I completely disperse in 1 liter of water at about 22–23° C within 20 seconds with vigorous shaking even after the formulation is left standing in the open for 10 days (in contrast, for example, to said "Monarch Teat Tabs", one 6-gram tablet left standing for 10 days taking 40 minutes to disperse in 2 liters of water at 25° C). Thus, the teat dip can be readily made up without waiting.

The pH and hardness of the water used to make the teat dip of this invention generally have relatively minor effects on the pH and titratable chlorine concentration of the solution. Highly alkaline water, the type commonly available as a water source on a farm, can be used. For example, a teat dip with a pH of 6.15 and 6115 ppm titratable chlorine was made from 30 grams formulation E of Table I using a liter of water having a pH of 8.7 and a hardness of 17 grains/gallon (291 mg/liter), and a teat dip with a pH of 6.1 and 6257 ppm titratable chlorine was made from 30 g of formulation E and a liter of water having a pH of 6.3 and a hardness of 78 grains/gallon (1333 mg/liter) with 1.5 ppm iron.

The teat dip of this invention will generally have an initial pH of 6 to 7.2, depending on the hardness of the particular water used. This pH will remain relatively stable when monosodium phosphate is in the formulation, it serving a dual purpose as a pH buffer. If the teat dip solution is not used the same day it is prepared (which is not the preferred practice), the pH will decrease, e.g., to about 5 in 9–10 days. The relatively low pH of the teat dip of this invention aids the killing of organisms, especially at relatively low ambient temperatures. The effectiveness of the teat dip also is relatively unaffected by the presence of organic material, including the emollient component in the formulation.

The above-described teat dip can be used in the same manipulative manner as teat dips heretofore proposed or used. Generally, teat dipping is carried out by immersing for several seconds at least one half to two thirds of the teat in a cup or other suitable container containing, for example, 250 ml of the teat dip. The same teat dip can be used to dip the teats of, for example, six cows, after which the teat dip can be discarded. Teat dipping is preferably used on lactating cows after each milking to destroy any pathogens remaining on the teats after milking and prevent or reduce infection from one milking to the next. In this manner, residual milk droplets are removed and the outside of the test as well as the teat canal openings are sanitized when they are most susceptible to invasion. The test dip can also be used on cows that are being dried off, in which case the teats are preferably dipped in the teat dip once a day for 3 to 4 days after the last milking. With freshening cows, dipping can be done twice daily, beginning about 3 days before calving.

As an example of the efficiency of the teat dip of this invention, a test was run in accordance with Protocol A as outlined by the Teat Dip Committee of the National Mastitis Council, Inc., Washington, D.C. (1973), using cows whose teats were experimentally contaminated with *Str. agalactae* suspended in milk. The teat dip (about 3,000 ppm titratable chlorine) made from formulation G of Table I was found to kill 95.0% of the bacteria, in contrast an 81.6% reduction in bacteria by a teat dip (6000 ppm titratable chlorine) at about pH 7.2, prepared from said Monarch Teat Tabs, thus showing the superior effectiveness of the teat dip of this invention. In another test run according to said Protocol A, a teat dip (about 3,000 ppm titratable chlorine and pH 6) made from formulation G of Table I killed 81.3% *Str. agalaceiae* and 95.2% *Staph. aureus* (as compared to a control, tap water, where the respective reductions were 36.2% and 59.5%). In still another test following said Protocol A, a teat dip (about 5,000 ppm titratable chlorine) prepared from formulation E of Table I was found to reduce the colony forming units of *Str. agalactiae* by 99.9% from the control (130 × 10$^6$ colony forming units) and of *Staph. aureus* by 99.6% from the control (80 × 10$^6$ colony forming units).

Teat dips containing about 5,000 ppm titratable chlorine prepared from formulation E of Table I were test evaluated in the field over periods ranging from 6 months to 1 year on a number of different farms where the cow herds ranged from 40 to 200 head. The farmers' comments on the effectiveness of said teat dips ranged from "we have less mastitis when we use it...irritation is no problem" to "helped our mastitis problems...no irritation which we blame to teat dip". For example, cultures on 216 udder quarters of one of the treated herds showed only 8.8% of the quarters suspect of sub-clinical infection, and cultures on 63 quarters of another of the treated herds showed only 9.5% suspect of subclinical infection — these values of 8.8 and 9.5% being far below the values for average herds. Following use of the teat dip, one of the farmers reported that his last WMT had a rating of 3 and another of the farmers reported his last WMT rating was 5. The WMT is the Wisconsin Mastitis Test, described in "Bovine Mastitis", by O. W. Schalm et al, Lea & Febiger Publishers, Phila., Pa., 1971, p. 141, a rating of 3 being a very low value (and thus very satisfactory), a rating of 5 being much better than average, a rating up to 10 being very good, and a rating of greater than 21 indicated a mastitis problem.

Various modifications and alternations of this invention will become apparent to those skilled in the art without departing from the scope and spirit of this invention.

What is claimed is:

1. A method for controlling bovine mastitis comprising immersing the teats of a cow in a teat dip comprising an aqueous dispersion of titratable chlorine produced by mixing with water a powdered, water-dispersible formulation containing an amount of chlorinated cyanurate sufficient to yield about 3,000 to 7,000 ppm titratable chlorine and a slightly acid to neutral or nearly neutral pH.

2. The method according to claim 1, wherein said cyanurate is powdered sodium dichloroisocyanurate and it is compounded with an amount of powdered carbon dioxide-producing adjuvant such that said formulation disperses completely in water in 30 seconds or less.

3. The method according to claim 2, wherein said carbon dioxide-producing adjuvant comprises sodium bicarbonate and monobasic sodium phosphate, and said teat dip contains an emollient selected from the group consisting of sorbitol, polyvinylpyrrolidone, and mixtures thereof.

4. The method according to claim 3, wherein said teat dip has a pH of 6.0 to 7.2 and contains about 5,000 ppm titratable chlorine.

5. A method according to claim 2 wherein the individual dual dosage units of 3,000 to 7,000 ppm titratable chlorine are separately packaged in sealed, relatively moisture- and gas-impermeable packages prior to said mixing with water.

6. A powdered, water-dispersible, effervescent formulation consisting essentially of 18 to 36 weight percent powdered sodium dichloroisocyanurate, 5 to 40 weight percent sodium sulfate, 0.5 to 2 weight percent liquid chlorinated paraffin with a chlorine content of about 40 weight percent, 5 to 15 weight percent polyvinylpyrrolidone, and 5 to 15 weight percent sorbitol, and 30 to 50 weight pecent of a mixture of 75 to 85 weight percent monobasic sodium phosphate and 15 to 25 weight percent of sodium bicarbonate, 30 grams of said formulation dispersing rapidly in one liter of water at 22° C with vigorous shaking in 30 seconds or less to produce an aqueous dispersion containing about 5,000 ppm titratable chlorine and having a pH of 6.0 to 6.2.

7. A teat dip comprising the formulation of claim 6 dispersed in water to form an aqueous dispersion containing about 5,000 ppm titratable chlorine.

8. An individually enclosed packaged, pre-measured amount of powder containing 3,000–7,000 ppm titratable chlorine when mixed with water to form a teat dip, said pre-measured amount comprising a powdered, water-dispersible formulation comprising powdered chlorinated cyanurate, powdered carbon dioxide-producing adjuvant, 0 to 5 weight percent liquid chlorinated paraffin, and an emollient amount of at least one emollient selected from the group consisting of sorbitol, polyvinylpyrrolidone, and mixtures thereof; 30 grams of said formulation dispersing rapidly in one liter of water at 22° C. in 30 seconds or less to produce a slightly acid to neutral aqueous dispersion containing about 3,000 to 7,000 ppm titratable chlorine.

9. The powdered formulation of claim 8 comprising 15 to 40 weight percent powdered sodium dichloroisocyanurate, 15 to 50 weight percent carbon dioxide-producing adjuvant, 0.1 to 5 weight percent liquid chlorinated paraffin containing about 30 to 60 weight percent chlorine, 5 to 15 weight percent polyvinylpyrrolidone, and 5 to 15 weight percent sorbitol.

* * * * *

UNITED STATES PATENT OFFICE
CERTIFICATE OF CORRECTION

Patent No. 4,025,628          Dated May 24, 1977

Inventor(s) Lloyd G. Dewey et al.

It is certified that error appears in the above-identified patent and that said Letters Patent are hereby corrected as shown below:

Column 1, line 30, "pyrolidone" should read --pyrrolidone--.
Column 1, line 30, "conjuction" should read --conjunction--.
Column 1, line 65, "dichloroisocyanaurate" should read
    --dichloroisocyanurate--.
Column 3, line 33, "predominantely" should read
    --predominantly--.
Column 4, line 35, "clori-" should read --chlori- --.
Column 4, line 42, "test" should read --teat--.
Column 5, line 41, "test" should read --teat--.
Column 5, line 54, "agalactae" should read --agalactiae--.
Column 5, line 50, "Protocol A" should be in quotes,
    --"Protocol A"--.
Column 5, line 59, "Monarch Teat Tabs" should be in quotes,
    --"Monarch Teat Tabs"--.
Column 5, lines 61 and 62, "Protocol A" should be in quotes,
    --"Protocol A"--.
Column 5, line 64, "agalaceiae" should read --agalactiae--.
Column 5, line 67, "Protocol A" should be in quotes,
    --"Protocol A"--.

UNITED STATES PATENT OFFICE
CERTIFICATE OF CORRECTION

Patent No. 4,025,628  Dated May 24, 1977

Inventor(s) Lloyd G. Dewey et al.

It is certified that error appears in the above-identified patent and that said Letters Patent are hereby corrected as shown below:

Column 6, line 23, "Wisconsin Mastitis Test" should be in quotes, --"Wisconsin Mastitis Test"--.
Column 6, line 25, "3" should be in quotes, --"3"--.
Column 6, line 26, "5" should be in quotes, --"5"--.
Column 6, line 41, "slighly" should read --slightly--.

Signed and Sealed this thirtieth Day of August 1977

[SEAL]

Attest:

RUTH C. MASON
Attesting Officer

C. MARSHALL DANN
Commissioner of Patents and Trademarks